(12) United States Patent
Matsunaga

(10) Patent No.: US 8,328,747 B2
(45) Date of Patent: Dec. 11, 2012

(54) KNEE BRACE

(75) Inventor: Satoshi Matsunaga, Izumi (JP)

(73) Assignee: Shilac Japan Inc., Izumisano (JP)

( * ) Notice: Subject to any disclaimer, the term of this patent is extended or adjusted under 35 U.S.C. 154(b) by 44 days.

(21) Appl. No.: 13/170,556

(22) Filed: Jun. 28, 2011

(65) Prior Publication Data

US 2011/0319800 A1 Dec. 29, 2011

(30) Foreign Application Priority Data

Jun. 28, 2010 (JP) ................................ 2010-146660

(51) Int. Cl.
*A61F 5/00* (2006.01)
(52) U.S. Cl. .............................. 602/26; 602/16; 602/23
(58) Field of Classification Search ................ 602/5, 16, 602/23, 26; 128/882
See application file for complete search history.

(56) References Cited

U.S. PATENT DOCUMENTS

| 5,024,216 | A | | 6/1991 | Shiono | |
| 5,857,988 | A | * | 1/1999 | Shirley | 602/26 |
| 6,436,066 | B1 | * | 8/2002 | Lockhart | 602/26 |
| 6,551,264 | B1 | * | 4/2003 | Cawley et al. | 602/16 |

FOREIGN PATENT DOCUMENTS

| JP | 2-111418 U | 9/1990 |
| JP | 4-126521 U | 11/1992 |
| JP | 2000197654 | 7/2000 |

OTHER PUBLICATIONS

Office Action dated Apr. 11, 2012 in corresponding Japanese Application No. 2010-146660.

* cited by examiner

*Primary Examiner* — Loan Thanh
*Assistant Examiner* — Camtu Nguyen
(74) *Attorney, Agent, or Firm* — Knobbe Martens Olson & Bear LLP

(57) ABSTRACT

The invention provides a knee stabilizing brace which is usable regardless of a damaged portion of a ligament of a knee joint. The knee stabilizing brace includes a brace body which has a back-side body portion applied to a back side of a thigh, a poples, and a back side of a crus, and right and left front-side body portions, which are applied to a front side of the thigh, a kneecap, and a front side of the crus, right and left support stays for reinforcement, and upper and lower fastening bands for fastening the brace body 1 around a thigh portion, wherein the brace body is fitted around a knee portion by overlapping and engaging surface fasteners of the right and left front-side body portions, four ring-like fasteners are provided on upper, lower, right, and left sides of the back side of the back-side body portion, four engaging regions are set to upper, lower, right, and left sides of the right and left front-side body portions, and first and second fastening bands for patella which are detachably engaged into one of the four ring-like fasteners and one of the four engaging regions are provided.

4 Claims, 12 Drawing Sheets

KNEE BRACE

BACKGROUND OF THE INVENTION

1. Field of the Invention

The present invention relates to a knee stabilizing brace used at the time of damage of a ligament of a knee joint.

2. Description of the Related Art

Knee stabilizing braces are used for damage of ligaments of knee joints and treating knee disease. For instance, a knee stabilizing brace disclosed in Japanese Unexamined Patent Publication No. 2000-197654 (paragraphs 0017 to 0020, FIGS. 1 to 3) has a knee brace body formed of a stretchable thick cloth, and a support stay for reinforcement arranged on either side of a knee. The support stay for reinforcement has an upper stay portion and a lower stay portion, and is inserted into and held by long bag-like support members 10 and 10'. The knee stabilizing brace can be fitted around a knee portion in a stable state by rear fastening belts 12 and 12', front fastening belts 15 and 15', and fastening bands for patella 18 and 18'.

Here, as shown in FIG. 3 of Japanese Unexamined Patent Publication No. 2000-197654, the rear fastening belt 12 has one end which is integrally fixed to the right bag-like support member 10, and the other end which is folded back by a ring-like fastener 13 provided to the left bag-like support member 10 and is engaged by a hook loop type fastener 14 provided at the distal end of the rear fastening belt 12, and the rear fastening belt 12' has one end which is integrally fixed to the right bag-like support member 10', and the other end which is folded back by the ring-like fastener 13 provided to the left bag-like support member 10' and is engaged by a hook loop type fastener 14 provided at the distal end of the rear fastening belt 12'. The front fastening belts 15 and 15' are engaged by the same means. The fastening bands for patella 18 and 18' extend diagonally upwardly from the lower ends on the front sides of the lower bag-like support members 10' and 10', and are engaged onto the surface of the knee brace body or the bag-like support members 10, 10 by hook loop type fasteners. The pair of fastening bands for patella 18 and 18' are fitted crosswise.

SUMMARY OF THE INVENTION

As the ligaments of a knee joint, an anterior cruciate ligament (ACL), a posterior cruciate ligament (PCL), a medial collateral ligament (MCL), and a lateral collateral ligament (LCL) are arranged on the front side, the back side, the inner side, and the outer side of the knee joint, respectively. When the fastening band for patella is fastened around a knee portion, there is a preferable strapping method according to the type of a damaged ligament. For instance, in the case of the PCL damage, there is a preferable method for strapping the fastening band, and in the case of the ACL damage, the fastening band need to be fastened by a strapping method different from the PCL damage.

However, in the above conventional art, each of the fastening bands for patella 18 and 18' has one end fixed onto a particular portion of the knee brace body, and can be used only for particular ligament damage. Therefore, a knee stabilizing brace corresponding to each damaged portion need to be prepared.

The present invention has been made in view of the above actual circumstances and an object of the present invention is to provide a knee stabilizing brace, usable regardless of the damaged portion of the ligament of a knee joint.

To solve the above problems, a knee stabilizing brace according to the present invention comprising:

a brace body which has a back-side body portion applied to a back side of a thigh, a poples, and a back side of a crus, and a right front-side body portion and a left front-side body portion, which are located on a right side and a left side of the back-side body portion and are applied to a front side of the thigh, a kneecap, and a front side of the crus, the brace body being formed of a material having flexibility;

a right support stay for reinforcement provided between the back-side body portion and the right front-side body portion;

a left support stay for reinforcement provided between the back-side body portion and the left front-side body portion;

an upper fastening band for fastening the brace body around a thigh portion; and a lower fastening band for fastening the brace body around a crus portion, wherein when the brace body is fitted around a knee portion, a surface fastener of the right front-side body portion and a surface fastener of the left front-side body portion are overlapped and engaged, the brace comprising:

a first ring-like fastener which is provided on the back side of the thigh in the back-side body portion and is provided near the right support stay;

a second ring-like fastener which is provided on the back side of the crus in the back-side body portion and is provided near the right support stay;

a third ring-like fastener which is provided on the back side of the thigh in the back-side body portion and is provided near the left support stay;

a fourth ring-like fastener which is provided on the back side of the crus in the back-side body portion and is provided near the left support stay;

a first engaging region which is set to the front side of the thigh in the right front-side body portion and is set near the right support stay;

a second engaging region which is set to the front side of the crus in the right front-side body portion and is set near the right support stay;

a third engaging region which is set to the front side of the thigh in the left front-side body portion and is set near the left support stay;

a fourth engaging region which is set to the front side of the crus in the left front-side body portion and is set near the left support stay;

a first fastening band for patella, which is detachably engaged between one selected from the four ring-like fasteners and one selected from the four engaging regions; and a second fastening band for patella, which is detachably engaged between another one selected from the four ring-like fasteners and another one selected from the four engaging regions.

The operation and effect of the knee stabilizing brace according to such a configuration will be described. The knee stabilizing brace is a brace preferably used, in particular, for damage of the ligament of a knee joint. As its main member, a brace body having a back-side body portion, a right front-side body portion, and a left front-side body portion is provided. The brace body is formed of a material having flexibility, and is fitted so as to surround a thigh and a crus including a knee. Support stays are arranged on the right and left sides of the knee portion for reinforcing the brace body. An upper fastening band and a lower fastening band are provided for fastening the brace body around the thigh portion and the crus portion.

Four ring-like fasteners are provided in the back-side body portion of the brace body. This is for detachably fitting (engaging) one end of the fastening band for patella. The four ring-like fasteners are arranged on the upper, lower, right, and left sides of the back-side body portion, and any one of the ring-like fasteners is selected according to a damaged ligament portion (for instance, PLC or ALC). Because two fastening bands for patella are provided, two of the four ring-like fasteners are selected. Further, in the present invention, the ring shape is not limited to a particular shape since it suffices to have a function of inserting the fastening band for patella therethrough. For instance, appropriate shapes such as a rectangular shape, an elliptical shape, and a circular shape can be adopted.

Four engaging regions are set to the right front-side body portion and the left front-side body portion of the brace body. This is for detachably engaging the other end of the fastening band for patella. The four engaging regions are set to the upper, lower, right, and left sides of the front-side body portions, and any one of the engaging regions is selected according to a damaged ligament portion. Because two fastening bands for patella are provided, two of the four engaging regions are selected.

Because the two detachable fastening bands for patella are provided in this manner so that the fastening bands for patella can be appropriately fastened according to a damaged ligament portion, a knee stabilizing brace need not be prepared according to each damaged portion. As a result, a knee stabilizing brace, usable regardless of the damaged portion of the ligament of a knee joint can be provided.

In the present invention, each of the four ring-like fasteners is coupled to the brace body via each of fitting sections made of cloth. Preferably, each of the arbitrary ring-like fasteners is capable of being detached by cutting each of the fitting sections.

When the brace is actually used, all the ring-like fasteners are not used. Accordingly, each of the unnecessary ring-like fasteners is capable of being detached by cutting each of the fitting sections.

In the present invention, preferably, each of the right support stay and the left support stay has an upper stay portion, a lower stay portion, a hinge portion which couples the upper stay portion and the lower stay portion, a bag-like upper holding cover which holds the upper stay portion to the brace body, and a bag-like lower holding cover which holds the lower stay portion to the brace body, and a space for enabling the first fastening band for patella or the second fastening band for patella to be inserted therethrough is formed between the hinge portion and the brace body.

The fastening band for patella is fitted (engaged) onto the engaging region on the front side and into the ring-like fastener on the back side. In this case, preferably, the position of the fastening band for patella to be fitted is stabilized. Accordingly, the fastening band is inserted through the space between the hinge portion and the brace body so that the position of the fastening band can be stabilized even when the knee is moved.

Preferably, each of the fitting sections according to the present invention is sewed onto the brace body so as to be overlapped with the upper holding cover or the lower holding cover. Accordingly, the sewing operation of the fitting section can be efficiently performed.

DETAILED DESCRIPTION OF THE PREFERRED EMBODIMENTS

Figure 1:
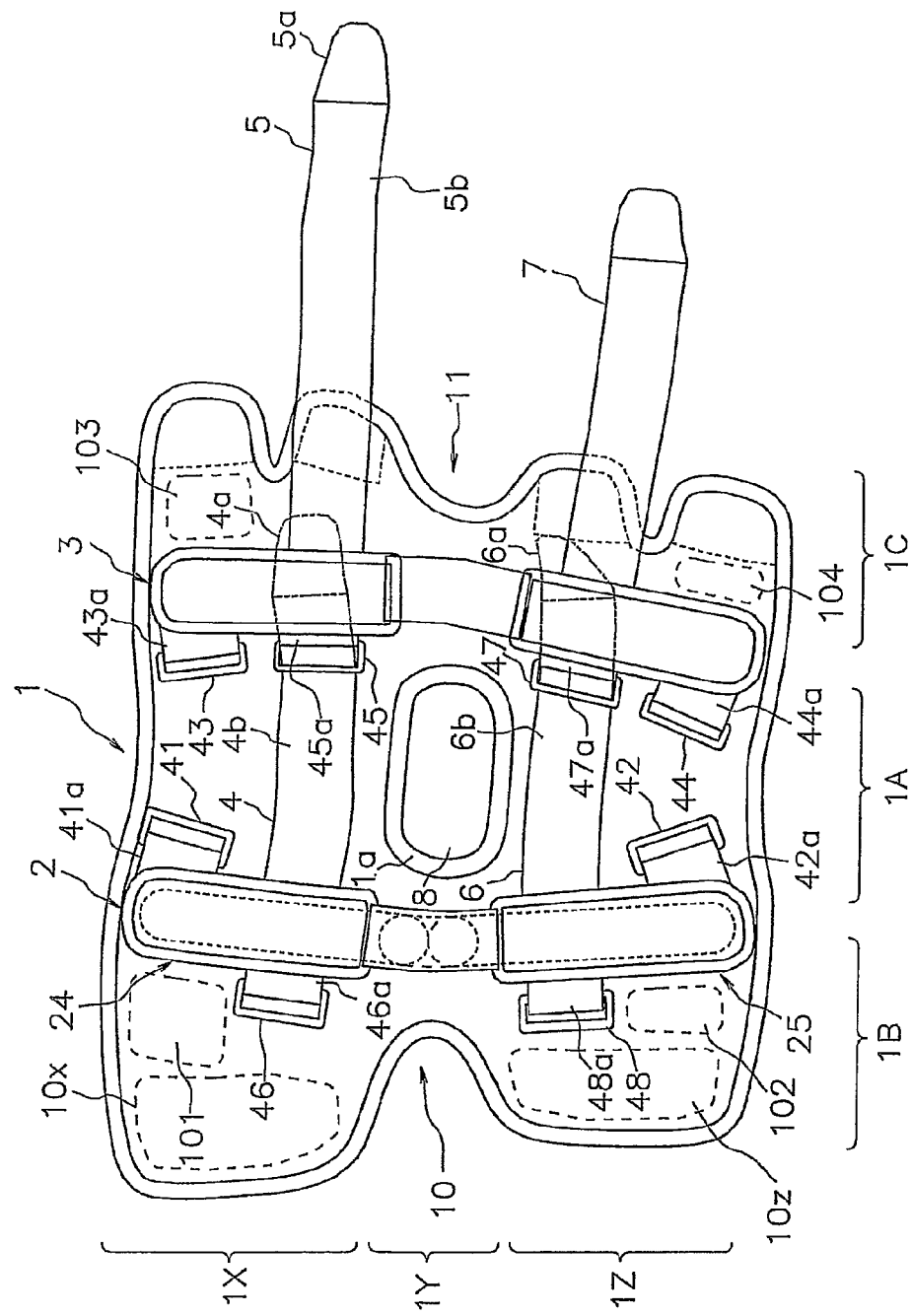
FIG. 1 is a diagram showing a front side in which a knee stabilizing brace is developed.
Figure 2:
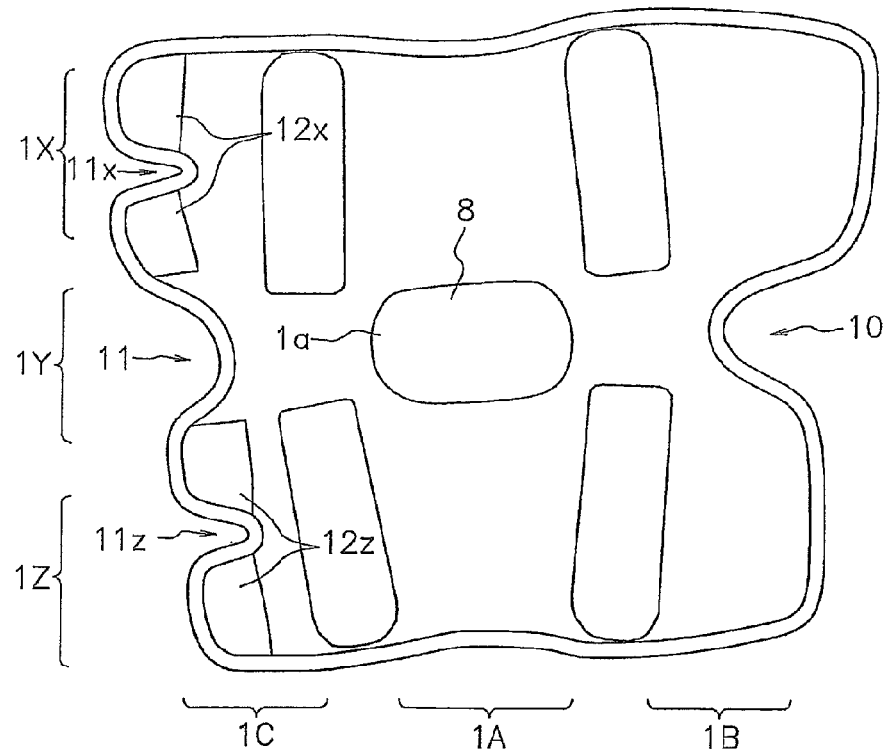
FIG. 2 is a diagram showing a back side in which a knee stabilizing brace is developed.
Figure 3:
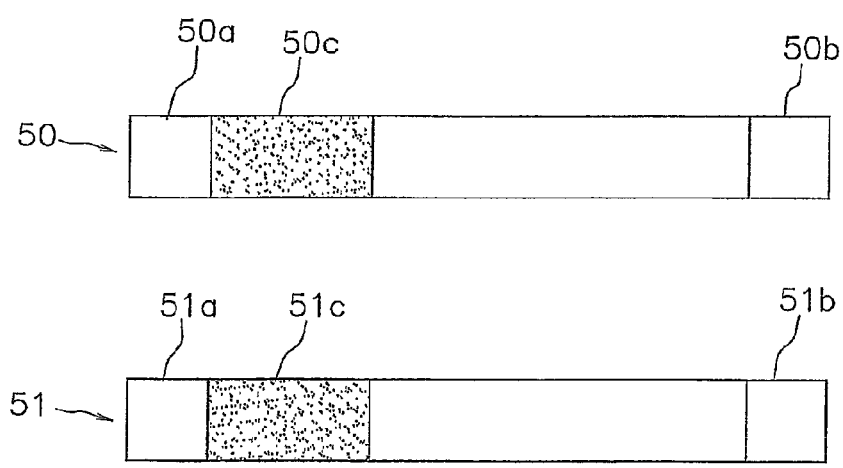
FIG. 3 is a diagram showing a first fastening band for patella and a second fastening band for patella.

A preferred embodiment of a knee stabilizing brace according to the present invention will be described with reference to the drawings. FIG. 1 is a diagram showing a front side (a side shown in outer appearance) in which the knee stabilizing brace is developed. FIG. 2 is a diagram showing a back side (a side applied to skin) in which the knee stabilizing brace is developed. FIG. 3 is a diagram showing a first fastening band for patella and a second fastening band for patella. In addition, FIGS. 1 and 2 are developed views in the state that the fastening bands for patella are detached.

Configuration of Knee Stabilizing Brace

A brace body 1 is formed of a stretchable material. The brace body 1 is largely horizontally divided into a back-side body portion 1A, a right front-side body portion 1B, and a left front-side body portion 1C, which are integrally formed. In addition, the brace body 1 is vertically divided into a thigh region 1X, a knee portion region 1Y, and a crus region 1Z.

The back side of the back-side body portion 1A shown in FIG. 2 is applied to the back side of a thigh, a poples, and the back side of a crus. In addition, the back sides of the right front-side body portion 1B and the left front-side body portion 1C, which are shown in FIG. 2, are applied to the front side of the thigh, a kneecap, and the front side of the crus. The entire surface on the front and back sides of the brace body 1 can exhibit the function of a surface fastener (hook-and-loop fastener).

A curved portion 10 which is recessed in a curved surface shape is formed in the right front-side body portion 1B of the brace body 1. A curved portion 11 which is recessed in a curved surface shape is formed in the left front-side body portion 1C thereof. When the brace body 1 is fitted around a knee portion, the curved portions 10 and 11 surround the kneecap. Further, a slit-like notch 11x is formed in the thigh region 1X of the left front-side body portion 1C, and likewise, a slit-like notch 11z is formed in the crus region 1Z.

As shown in FIG. 2, hook type surface fasteners 12x are formed on the upper and lower sides of the notch 11x, and hook type surface fasteners 12z are formed on the upper and lower sides of the notch 11z. When the brace is fitted, the surface fasteners 12x of the thigh region 1X can be detachably engaged onto an engaging region 10x on the front side of the right front-side body portion 1B. In addition, likewise, the surface fasteners 12z of the crus region 1Z can be detachably engaged onto an engaging region 10z on the front side of the right front-side body portion 1C.

Configuration of Support Stays

As shown in FIGS. 1 and 2, a right support stay 2 for reinforcement is provided between the back-side body portion 1A and the right front-side body portion 1B, and a left support stay 3 for reinforcement is provided between the back-side body portion 1A and the left front-side body portion 1C. The right support stay 2 and the left support stay 3 have the same configuration. Only the right support stay 2 will be described with reference to FIGS. 4A and 4B, and the description of the configuration of the left support stay 3 will not be given.

Figure 4:
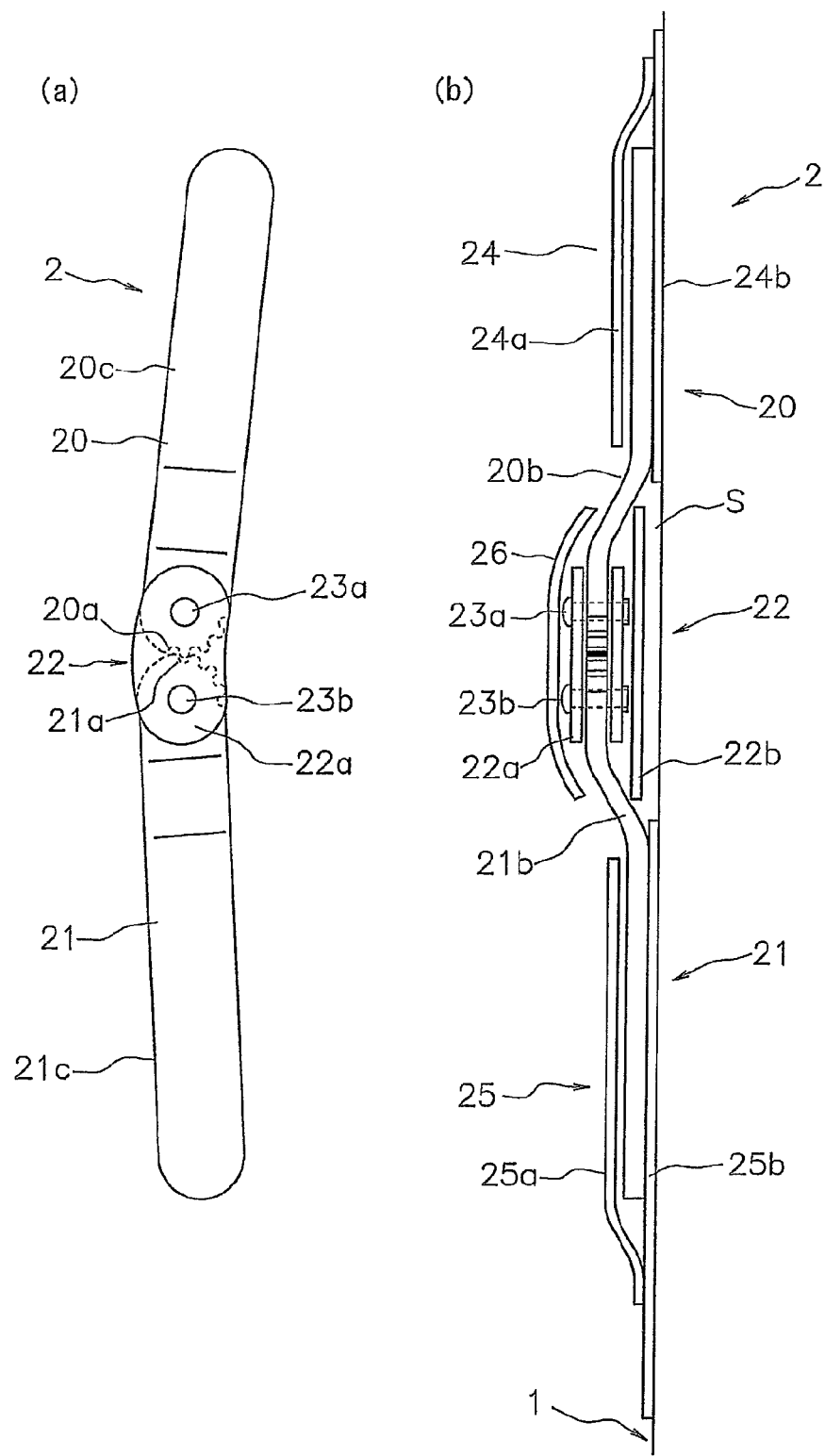
FIGS. 4A and 4B are diagrams showing a configuration of a support stay.

FIG. 4A is a plan view showing the configuration of the support stay, and FIG. 4B is a side view showing the configuration of the support stay. The support stay 2 has an upper stay portion 20, a lower stay portion 21, and a hinge portion 22 for coupling the upper stay portion 20 and the lower stay portion 21. The upper stay portion 20 and the lower stay portion 21 can be formed by press molding a metal plate of aluminum and the like, and have ends integrally formed with gear portions 20a and 21a, respectively, to configure the hinge portion 22. The gear portions 20a and 21a are meshed so that the upper stay portion 20 and the lower stay portion 21 can rotate so as to follow the movement of the knee.

A pair of holding plates 22a and 22b for holding the upper and lower stay portions 20 and 21 are provided, and hold the gear portions 20a and 21a sandwiched therebetween. In addition, a grommet shaft 23a is provided at the center of rotation of the gear portion 20a, and a grommet shaft 23b is provided at the center of rotation of the gear portion 21a, thereby rotatably holding the gear portions 20a and 21a.

Diagonally bending portions 20b and 21b are provided in the upper stay portion 20 and the lower stay portion 21, respectively, so that the hinge portion 22 is slightly raised from the surface of the brace body 1. Accordingly, a space S is formed between the hinge portion 22 and the brace body 1. This functions as a space for inserting the first and second fastening bands for patella therethrough.

A rod-like body portion 20c of the upper stay portion 20 is inserted into an upper holding cover 24, and a rod-like body portion 21c of the lower stay portion 21 is inserted into a lower holding cover 25. In the upper holding cover 24, a front-side body cover portion 24a and a back-side body cover portion 24b are both sewed onto the brace body 1, and a bag-like insertion hole for inserting the body portion 20c thereinto is formed. Likewise, in the lower holding cover 25, a front-side body cover portion 25a and a back-side body cover portion 25b are both sewed onto the brace body 1, and a bag-like insertion hole for inserting the body portion 21c thereinto is formed. A tubular body cover 26 is provided so as not to expose the hinge portion 22.

Arrangement Configuration of Ring-Like Fasteners

As shown in FIG. 1, a total of eight ring-like fasteners are provided on the front side of the brace body 1. A first ring-like fastener 41 is provided in the thigh region 1X in the back-side body portion 1A, and is provided near the right support stay 2.

A second ring-like fastener 42 is provided in the crus region 1Z in the back-side body portion 1A, and is provided near the right support stay 2. A third ring-like fastener 43 is provided in the thigh region 1X in the back-side body portion 1A, and is provided near the left support stay 3. A fourth ring-like fastener 44 is provided in the crus region 1Z in the back-side body portion 1A, and is provided near the left support stay 3. The four ring-like fasteners 41 to 44 are provided for fitting the fastening bands for patella.

Figure 5:
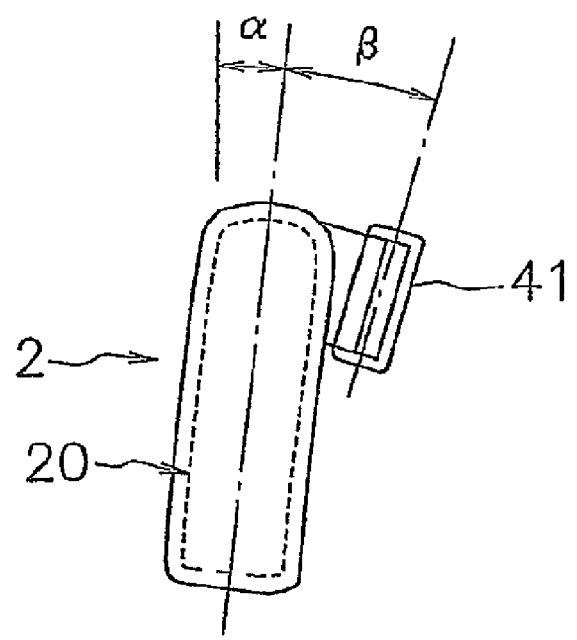
FIG. 5 is a diagram showing an attaching angle of the support stay and an attaching angle of a ring-like fastener.

FIG. 5 is a diagram for describing the attaching angle of the support stays 2 and 3 and the attaching angle of the ring-like fastener 41. The upper stay portion 20 of the right support stay 2 is inclined at substantially an angle $\alpha$ with respect to a vertical line. In addition, the first ring-like fastener 41 is attached so as to be inclined at substantially an angle $\beta$ with respect to the upper stay portion 20. The angle $\alpha$ is an angle set in order that the knee stabilizing brace is easily fitted around the knee portion in a natural state. The angle $\beta$ is an angle set for strapping fastening bands for patella 50 and 51 described later at a natural angle.

Next, a fifth ring-like fastener 45 is provided in the thigh region 1X in the back-side body portion 1A, and is provided near the left support stay 3. In addition, the fifth ring-like fastener 45 is located below the third ring-like fastener 43. A first upper fastening band 4 for fastening the brace body 1 around the thigh portion is provided. One end of the first upper fastening band 4 is sewed onto the brace body 1 together with the upper holding cover 24. The entire surface of the first upper fastening band 4 can function as a surface fastener. An end 4a of the first upper fastening band 4 is inserted through the fifth ring-like fastener 45, and is folded back to be overlapped with an engaging region 4b so that fastening can be performed.

A sixth ring-like fastener 46 is provided in the thigh region 1X in the right front-side body portion 1B, and is provided near the right support stay 2. The sixth ring-like fastener 46 is provided so as to be located at the same height as the fifth ring-like fastener 45. A second upper fastening band 5 for fastening the brace body 1 around the thigh portion is provided. The entire surface of the second upper fastening band 5 can function as a surface fastener. An end 5a of the second upper fastening band 5 is inserted through the sixth ring-like fastener 46, and is folded back to be overlapped with an engaging region 5b so that fastening can be performed.

A seventh ring-like fastener 47 is provided in the crus region 1Z in the back-side body portion 1A, and is provided near the left support stay 3. In addition, the seventh ring-like fastener 47 is located above the fourth ring-like fastener 44. A first lower fastening band 6 for fastening the brace body 1 around the crus portion is provided. One end of the first lower fastening band 6 is sewed onto the brace body 1 together with the lower holding cover 25. The entire surface of the first lower fastening band 6 can function as a surface fastener. An end 6a of the first lower fastening band 6 is inserted through the seventh ring-like fastener 47, and is folded back to be overlapped with an engaging region 6b so that fastening can be performed.

An eighth ring-like fastener 48 is provided in the crus region 1Z in the right front-side body portion 1B, and is provided near the right support stay 2. The eighth ring-like fastener 48 is provided so as to be located at the same height as the seventh ring-like fastener 47. A second lower fastening band 7 for fastening the brace body 1 around the crus portion is provided. The entire surface of the second lower fastening band 7 can function as a surface fastener. An end 7a of the second lower fastening band 7 is inserted through the eighth ring-like fastener 48, and is folded back to be overlapped with an engaging region 7b so that fastening can be performed.

Each of the fifth to eighth ring-like fasteners 45 to 48 is attached so that its attaching angle is parallel or substantially parallel with the upper stay portion 20 or the lower stay portion 21. As described above, the knee stabilizing brace is strongly fitted around the thigh portion and the crus portion by the four fastening bands 4 to 7.

Each of the first to fourth ring-like fasteners 41 to 44 is attached to the brace body 1 by each of fitting sections 41a to 44a. In this case, each of the fitting sections 41a to 44a is sewed onto the brace body 1 so as to be overlapped with the upper holding cover 24 or the lower holding cover 25. Each of the fitting sections 41a to 44a is made of a cloth, and can be cut by scissors or a cutter. Each of the fitting sections 41a to 44a is cut so that each of the arbitrary ring-like fasteners 41 to 44 is capable of being detached from the brace body 1.

In addition, each of the fifth to eighth ring-like fasteners 45 to 48 is attached to the brace body 1 by each of fitting sections 45a to 48a. Each of the fitting sections 45a to 48a is also sewed onto the brace body 1 so as to be overlapped with the upper holding cover 24 or the lower holding cover 25. In this manner, since each of the fitting sections 45a to 48a is sewed so as to be overlapped with the upper holding cover 24 or the lower holding cover 25, the sewing operation can be simplified.

A hole 1a is formed in the center portion of the brace body 1, and an elastic cloth 8 with high air permeability is sewed. The hole 1a is a portion applied to the poples when the brace is fitted, and is provided in a sweatable location. Accordingly, the cloth 8 with high air permeability is applied so that no uncomfortable feeling can be caused.

Arrangement of Engaging Regions

Four engaging regions for engaging the fastening bands for patella 50 and 51 are set to the right front-side body portion 1B and the left front-side body portion 1C.

A first engaging region 101 is set to the thigh region 1X in the right front-side body portion 1B, and is set near the right support stay 2. The first engaging region 101 is located above the sixth ring-like fastener 46. A second engaging region 102 is set to the crus region 1Z in the right front-side body portion 1B, and is set near the right support stay 2. The second engaging region 102 is located below the eighth ring-like fastener 48. A third engaging region 103 is set to the thigh region 1X in the left front-side body portion 1C, and is set near the left support stay 3. The third engaging region 103 is located above the fixed end of the second upper fastening band 5. A fourth engaging region 104 is set to the crus region 1Z in the left front-side body portion 1C, and is set near the left support stay 3. The fourth engaging region 104 is located below the fixed end of the second lower fastening band 7.

Configuration of Fastening Bands for Patella

Next, the first fastening band for patella 50 and the second fastening band for patella 51 will be described with reference to FIG. 3. The fastening bands for patella 50 and 51 have the same shape. The first fastening band for patella 50 has, at one end, a first surface fastener 50a in a hook shape, and, at the other end, a second surface fastener 50b in a hook shape. A third surface fastener 50c which is adjacent to the first surface fastener 50a and has a loop shape for folding back and engaging the first surface fastener 50a is provided. Likewise, the second fastening band for patella 51 has a first surface fastener 51a, a second surface fastener 51b, and a third surface fastener 51c.

Each of the first surface fasteners 50a and 51a is inserted through and is engaged into any one of the first ring-like fastener 41 to the fourth ring-like fastener 44. Each of the second surface fasteners 50b and 51b is engaged onto any one of the first engaging region 101 to the fourth engaging region 104. With which of the ring-like fasteners 41 to 44 the first surface fastener 50a or 51a is engaged and onto which of the engaging regions 101 to 104 the second surface fastener 50b or 51b is engaged are determined according to the damaged portion of the ligament of a knee joint.

Fitting Procedures of Brace

Figure 6:
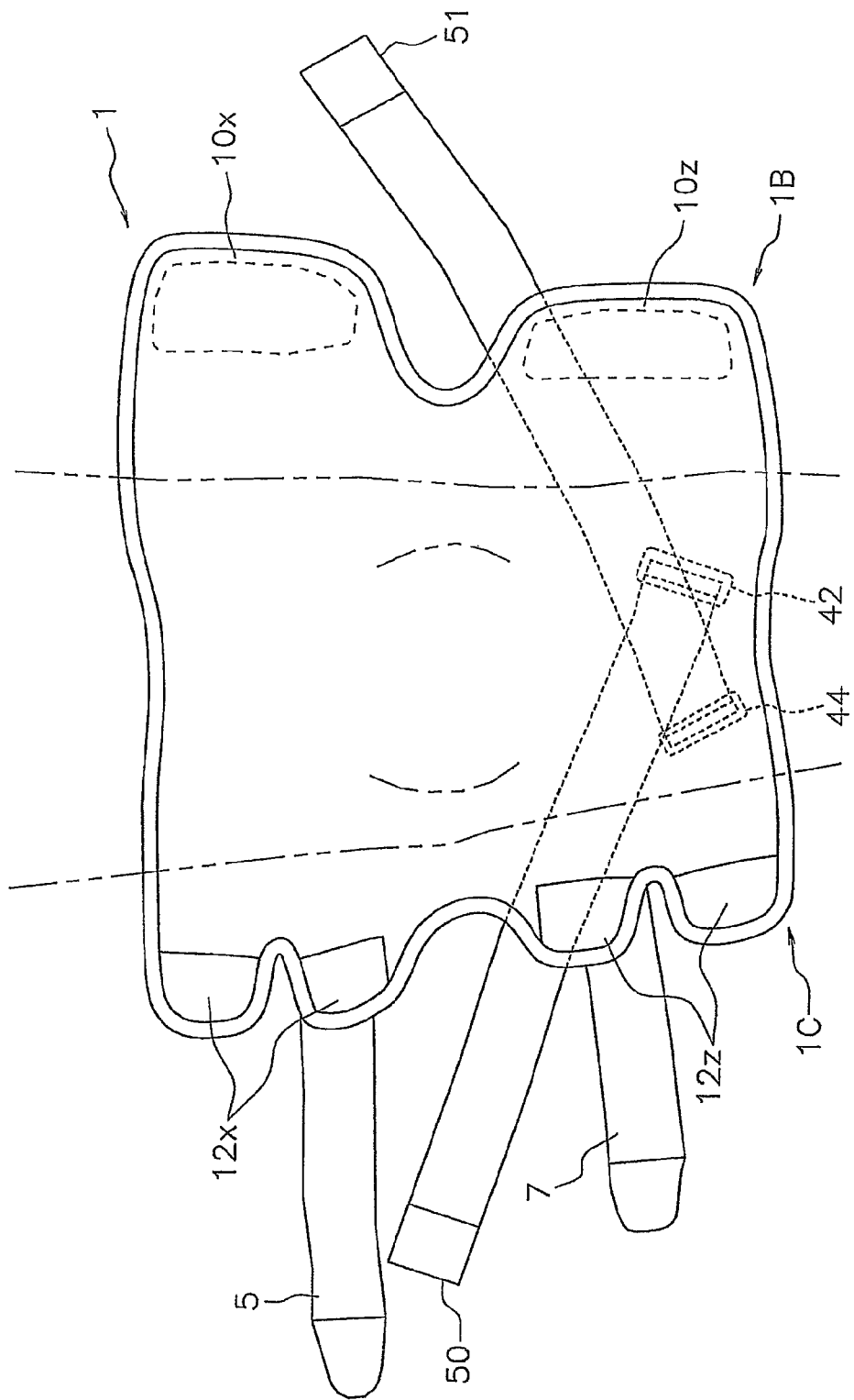
FIG. 6 is a diagram showing a fitting procedure of the brace (in the case of PCL damage)

Next, fitting procedures of the brace according to the present embodiment will be described. It should be noted that the right leg brace and the left leg brace are the same. In the description of FIG. 6 and thereafter, fitting procedures of the right leg brace will be described, which are the same for the left leg brace.

As shown in FIG. 6, the back side of the back-side body portion 1A of the brace body 1 is applied to the back side of the knee portion (the poples side). In this example, the fitting of the brace corresponding to the PCL damage will be described. In this case, preferably, one end of the first fastening band for patella 50 is previously fitted into the second ring-like fastener 42, and one end of the second fastening band for patella 51 is previously fitted into the fourth ring-like fastener 44.

Figure 7:
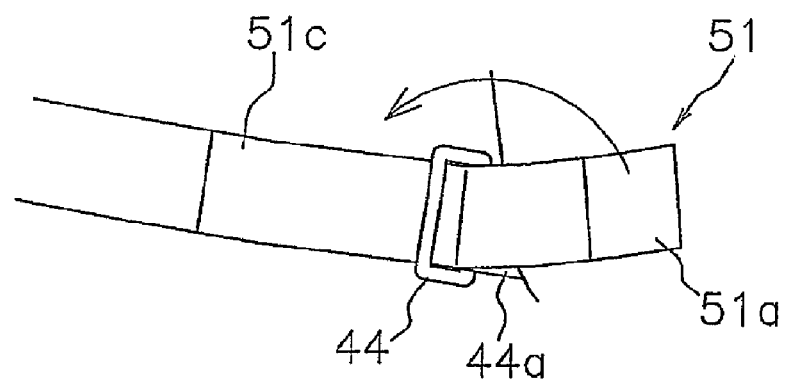
FIGS. 7A and 7B are diagrams showing a fitting procedure of the brace.
Figure 7:
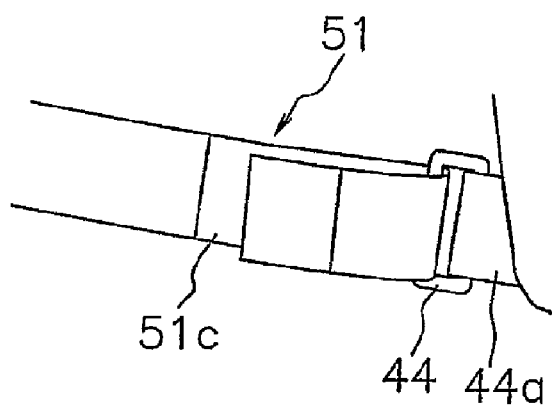

FIGS. 7A and 7B are partially enlarged views showing a procedure of fitting (engaging) the second fastening band for patella 51 into the fourth ring-like fastener 44. First, the end of the second fastening band for patella 51 is inserted through the fourth ring-like fastener 44 to fold back the portion of the surface fastener 51a. Next, the surface fastener 51a and the surface fastener 51c are engaged. This method is the same for the first fastening band for patella 50, and is also the same for when fitting into other ring-like fasteners 41 to 43.

Figure 8:
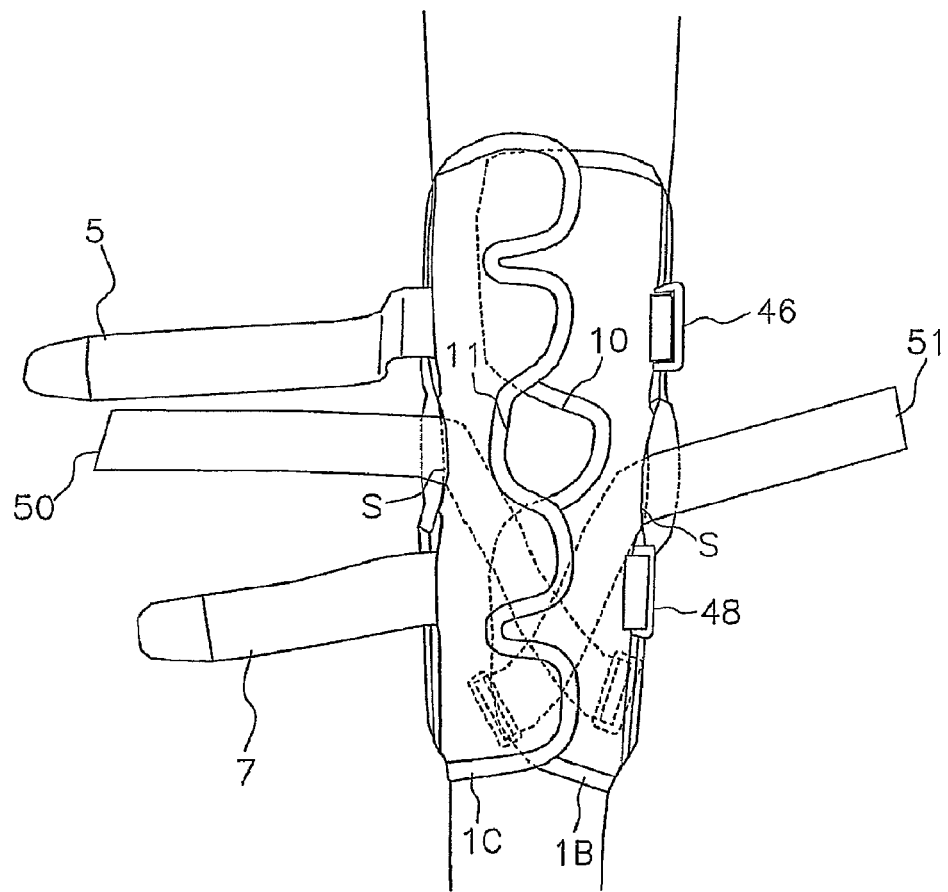
FIG. 8 is a diagram showing a fitting procedure of the brace.

FIG. 8 shows the state that the right front-side body portion 1B and the left front-side body portion 1C are folded back and overlapped on the front side of the knee. Because the brace body 1 has stretchability, the left front-side body portion 1C is overlapped onto the right front-side body portion 1B so as to be fitted around the knee. Accordingly, the surface fasteners 12x and 12z provided on the back side of the left front-side body portion 1C are engaged onto the engaging regions 10x and 10z on the front side of the right front-side body portion 1B. At this time, the kneecap is exposed from the right and left curved portions 10 and 11.

Figure 9:
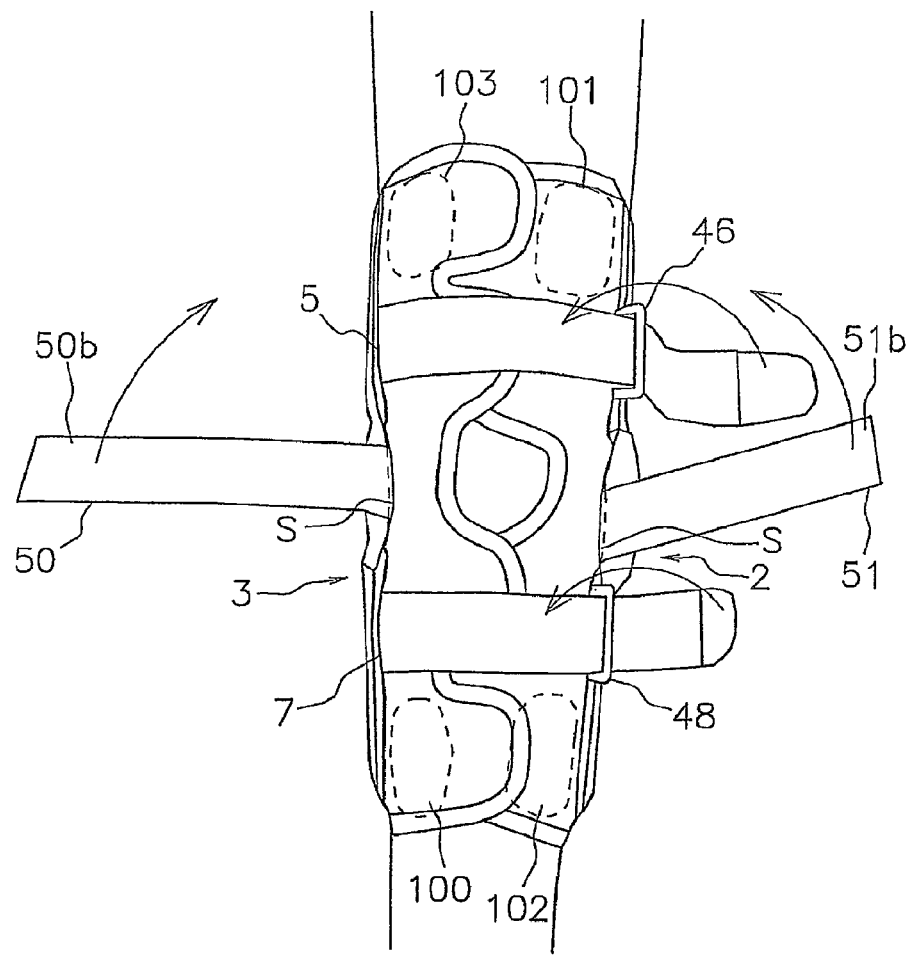
FIG. 9 is a diagram showing a fitting procedure of the brace.

As shown in FIGS. 8 and 9, the second upper fastening band 5 is fastened around the thigh portion by inserting its end into the sixth ring-like fastener 46. In addition, the second lower fastening band 7 is fastened around the crus portion by inserting its end into the eighth ring-like fastener 48. The fastening method of these fastening bands is as described in FIGS. 7A and 7B.

Although not shown in the drawings, the first upper fastening band 4 on the back side of the knee portion is fastened around the thigh portion by inserting its end into the fifth ring-like fastener. In addition, the first lower fastening band 6 is fastened around the crus portion by inserting its end into the seventh ring-like fastener. In this manner, the fastening bands 4 to 7 are fastened around the thigh portion and the crus portion from the front and back sides. The fastening order of each of the fastening bands 4 to 7 may be performed according to preference.

Next, the fitting of the first fastening band for patella 50 and the second fastening band for patella 51 will be described. The first fastening band for patella 50 is previously inserted through the space S formed between the left support stay 3 and the brace body 1. The second fastening band for patella 51 is previously inserted through the space S formed between the right support stay 2 and the brace body 1.

Figure 10:
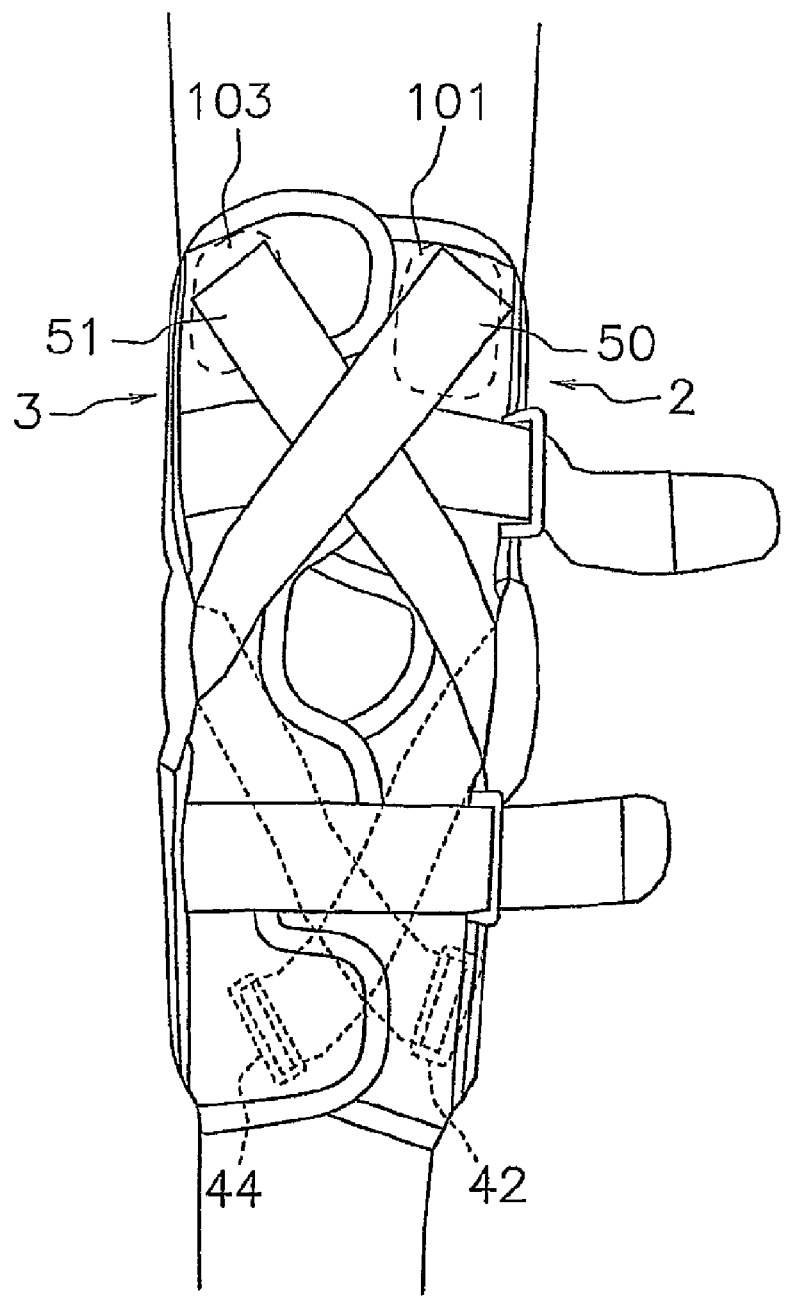
FIG. 10 is a diagram showing a fitting completed state of the brace (in the case of the PCL damage)

As shown in FIG. 10, the surface fastener 50b formed at the end of the first fastening band for patella 50 is engaged onto the first engaging region 101. The surface fastener 51b formed at the end of the second fastening band for patella 51 is engaged onto the third engaging region 103. Accordingly, the fitting of the brace in the case of the PCL damage is completed. The first fastening band for patella 50 and the second fastening band for patella 51 cross each other, but any of them may be above.

In the Case of ACL Damage

Figure 11:
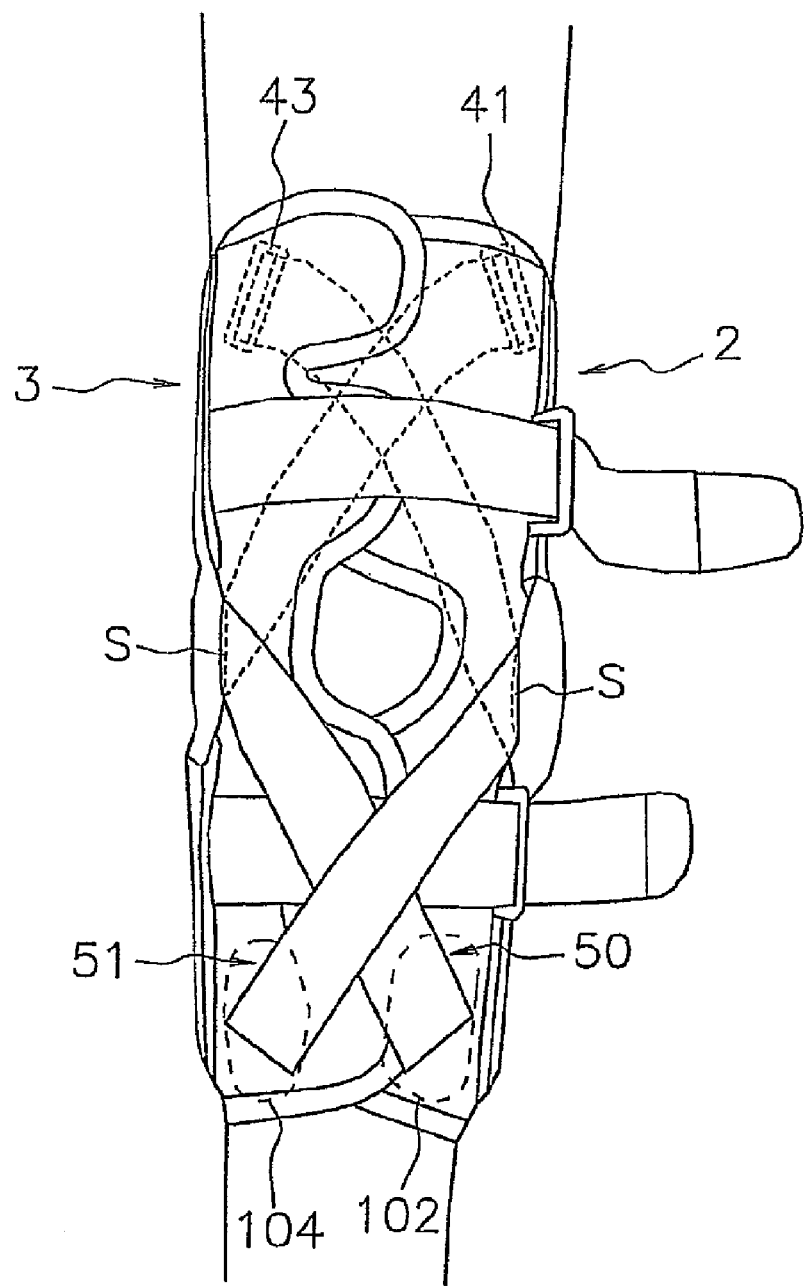
FIG. 11 is a diagram showing a fitting completed state of the brace (in the case of ACL damage)

FIG. 11 shows a fastening method of the first fastening band for patella 50 and the second fastening band for patella 51 in the case of the ACL damage. Similar to the case in FIG. 10, the state that the right leg is seen from the front is shown. One end of the first fastening band for patella 50 is engaged into the first ring-like fastener 41, and the other end thereof is engaged onto the second engaging region 102 after being inserted through the space S of the left support stay 3 in the midway. One end of the second fastening band for patella 51 is engaged into the third ring-like fastener 43, and the other end thereof is engaged onto the fourth engaging region 104 after being inserted through the space S of the right support stay 2 in the midway. The left leg brace is fitted in the same manner.

In the Case of MCL Damage

Figure 12:
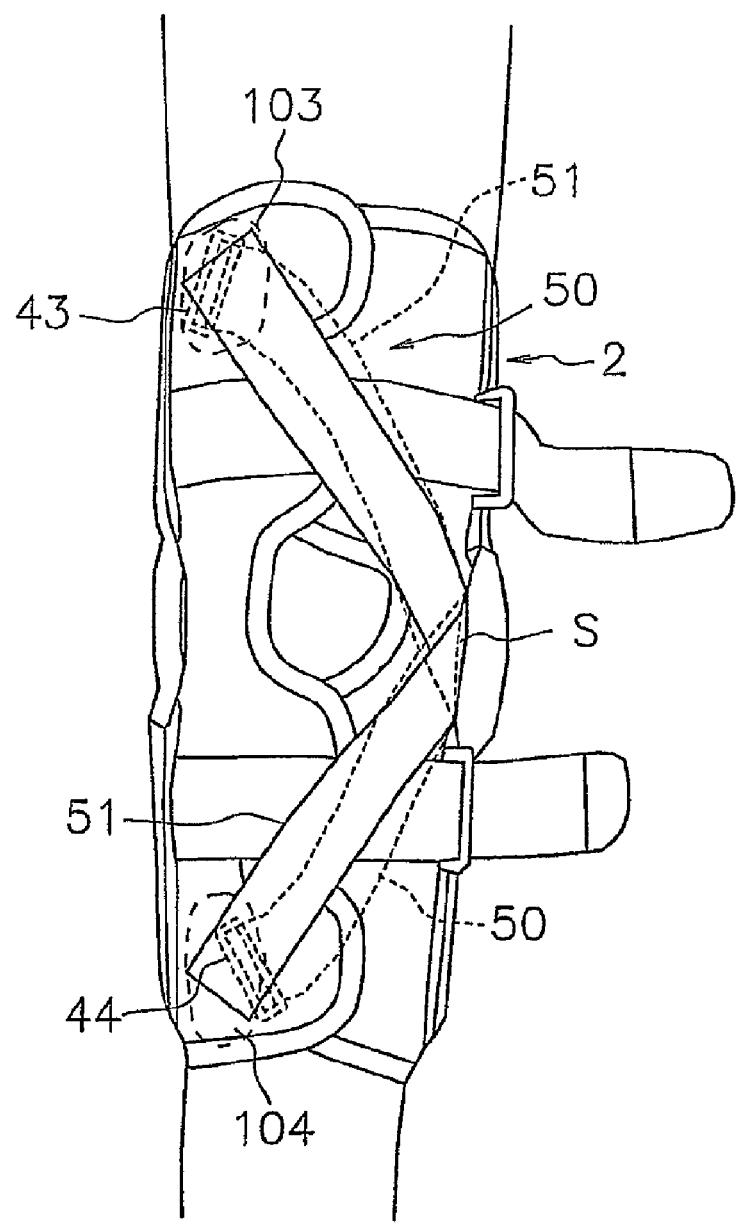
FIG. 12 is a diagram showing a fitting completed state of the brace (in the case of MCL damage)

FIG. 12 shows a fastening method of the first fastening band for patella 50 and the second fastening band for patella 51 in the case of the MCL damage. Similar to the case in FIG. 10, the state that the right leg is seen from the front is shown. One end of the first fastening band for patella 50 is engaged into the fourth ring-like fastener 44, and the other end thereof is engaged onto the third engaging region 103 after being inserted through the space S of the right support stay 2 in the midway. One end of the second fastening band for patella 51 is engaged into the third ring-like fastener 43, and the other end thereof is engaged onto the fourth engaging region 104 after being also inserted through the space S of the right support stay 2 in the midway. In other words, the brace is fitted so as to pull the inner side of the knee outwardly. Therefore, the first fastening band for patella 50 and the second fastening band for patella 51 are fastened so that they are symmetrical between the right leg and the left leg.

In the Case of LCL Damage

Figure 13:
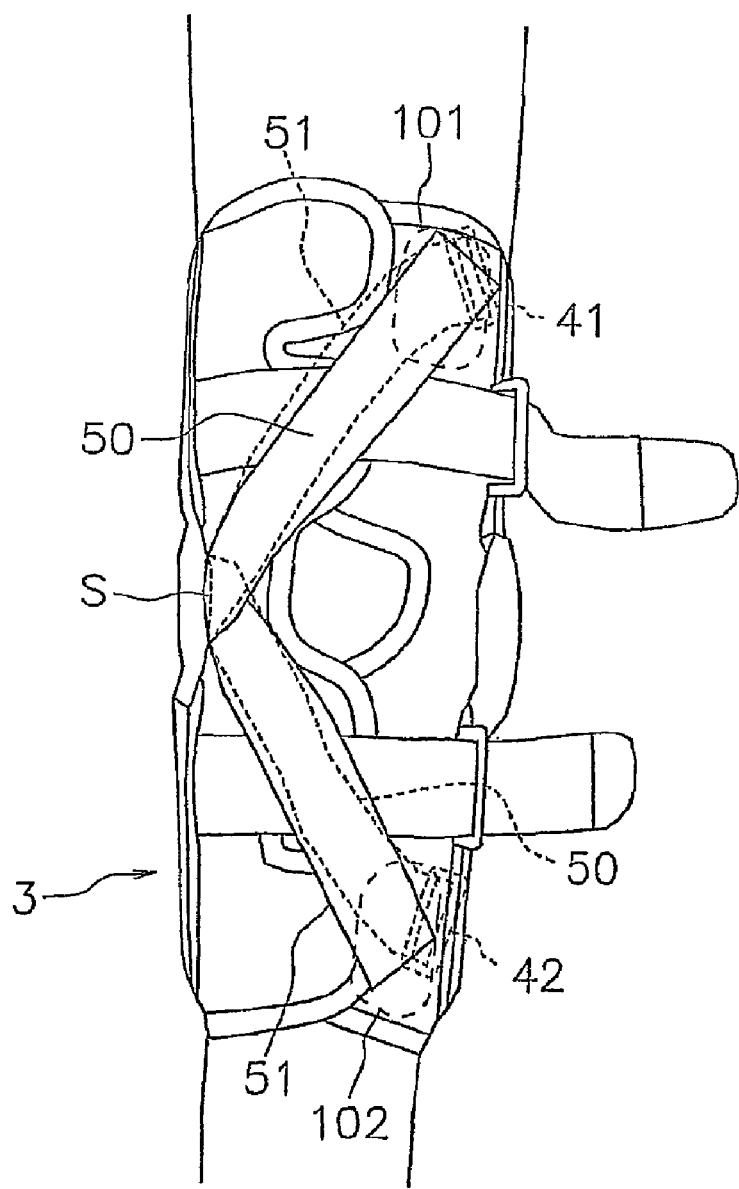
FIG. 13 is a diagram showing a fitting completed state of the brace (in the case of LCL damage).

FIG. 13 shows a fastening method of the first fastening band for patella 50 and the second fastening band for patella 51 in the case of the LCL damage. Similar to the case in FIG. 10, the state that the right leg is seen from the front is shown. One end of the first fastening band for patella 50 is engaged into the second ring-like fastener 42, and the other end thereof is engaged onto the first engaging region 101 after being inserted through the space S of the left support stay 3 in the midway. One end of the second fastening band for patella 51 is engaged into the first ring-like fastener 41, and the other end thereof is engaged onto the second engaging region 102 after being also inserted through the space S of the left support stay 3 in the midway. In other words, the brace is fitted so as to pull the outer side of the knee inwardly. Therefore, the first fastening band for patella 50 and the second fastening band for patella 51 are fastened so that they are symmetrical between the right leg and the left leg.

According to the above configuration, one brace can cope with the four damages of PCL, ACL, MCL, and LCL. In any case, two of the four ring-like fasteners 41 to 44 are actually used, and the remaining two ring-like fasteners are not used. In this case, when each of the fitting sections 41a to 44a connecting each of the ring-like fasteners 41 to 44 to the brace body 1 is cut, each of the unnecessary ring-like fasteners can be removed from the brace body 1. Whether or not each of the fitting sections 41a to 44a is cut can be arbitrarily performed according to the preference of the user.

Another Embodiment

The ring shape of the ring-like fasteners according to the present invention is not limited to a particular shape because it suffices to have the function of inserting the fastening band therethrough. For instance, appropriate shapes such as a rectangular shape, an elliptical shape, and a circular shape can be adopted.

In the present embodiment, two upper fastening bands and two lower fastening bands are provided, however, the present invention is not limited thereto, and one upper fastening band and one lower fastening band may be provided.

When the right front-side body portion and the left front-side body portion are overlapped and engaged in order to fit the brace body, any one of them may be above. In addition, the shape of the overlapped portion can be variously changed.

The engagement of the surface fasteners is enabled by combining the hook-shaped surface fastener and the loop-shaped surface fastener, but other types may also be used.

1 brace body
1A back-side body portion
1B right front-side body portion
1C left front-side body portion
1X thigh region
1Y knee portion region
1Z crus region
2 right support stay
3 left support stay
4 first upper fastening band
5 second upper fastening band
6 first lower fastening band
7 second lower fastening band
24 upper holding cover
25 lower holding cover
41 first ring-like fastener
41a fitting section
42 second ring-like fastener
42a fitting section
43 third ring-like fastener
43a fitting section
44 fourth ring-like fastener
44a fitting section
50 first fastening band for patella
51 second fastening band for patella
101 first engaging region
102 second engaging region 103 third engaging region
104 fourth engaging region
S space

What is claimed is:

1. A knee stabilizing brace comprising:
a brace body which has a back-side body portion applied to a back side of a thigh, a poples, and a back side of a crus, and a right front-side body portion and a left front-side body portion, which are located on a right side and a left side of the back-side body portion and are applied to a front side of the thigh, a kneecap, and a front side of the crus, the brace body being formed of a material having flexibility;
a right support stay for reinforcement provided between the back-side body portion and the right front-side body portion;
a left support stay for reinforcement provided between the back-side body portion and the left front-side body portion;
an upper fastening band for fastening the brace body around a thigh portion; and
a lower fastening band for fastening the brace body around a crus portion, wherein
when the brace body is fitted around a knee portion, a surface fastener of the right front-side body portion and a surface fastener of the left front-side body portion are overlapped and engaged, the brace comprising:
a first ring-like fastener which is provided on the back side of the thigh in the back-side body portion and is provided near the right support stay;
a second ring-like fastener which is provided on the back side of the crus in the back-side body portion and is provided near the right support stay;
a third ring-like fastener which is provided on the back side of the thigh in the back-side body portion and is provided near the left support stay;
a fourth ring-like fastener which is provided on the back side of the crus in the back-side body portion and is provided near the left support stay;
a first engaging region which is set to the front side of the thigh in the right front-side body portion and is set near the right support stay;
a second engaging region which is set to the front side of the crus in the right front-side body portion and is set near the right support stay;
a third engaging region which is set to the front side of the thigh in the left front-side body portion and is set near the left support stay;
a fourth engaging region which is set to the front side of the crus in the left front-side body portion and is set near the left support stay;
a first fastening band for patella, which is detachably engaged between one selected from the four ring-like fasteners and one selected from the four engaging regions; and
a second fastening band for patella, which is detachably engaged between another one selected from the four ring-like fasteners and another one selected from the four engaging regions.

2. The knee stabilizing brace according to claim 1, wherein each of the four ring-like fasteners is coupled to the brace body via each of fitting sections made of cloth, and each of the arbitrary ring-like fasteners is capable of being detached by cutting each of the fitting sections.

3. The knee stabilizing brace according to claim 2, wherein each of the fitting sections is sewed onto the brace body so as to be overlapped with the upper holding cover or the lower holding cover.

4. The knee stabilizing brace according to claim 1, wherein each of the right support stay and the left support stay has an upper stay portion, a lower stay portion, a hinge portion which couples the upper stay portion and the lower stay portion, a bag-like upper holding cover which holds the upper stay portion to the brace body, and a bag-like lower holding cover which holds the lower stay portion to the brace body, and a space for enabling the first fastening band for patella or the second fastening band for patella to be inserted therethrough is formed between the hinge portion and the brace body.

\* \* \* \* \*